United States Patent
Meneses et al.

(10) Patent No.: US 10,849,333 B2
(45) Date of Patent: Dec. 1, 2020

(54) DEVICES AND METHODS FOR PASTEURIZING AND/OR STERILIZING PARTICULATE MATERIAL, AND CARTRIDGE

(71) Applicant: BÜHLER AG, Uzwil (CH)

(72) Inventors: Nicolas Meneses, Gossau (CH); Martin Hersche, St. Gallen (CH); Alasdair Currie, London (GB); Niklaus Schönenberger, Herisau (CH); Thomas Scheiwiller, Zuzwil (CH)

(73) Assignee: BUEHLER AG, Uzwil (CH)

( * ) Notice: Subject to any disclaimer, the term of this patent is extended or adjusted under 35 U.S.C. 154(b) by 0 days.

(21) Appl. No.: 16/326,800

(22) PCT Filed: Aug. 17, 2017

(86) PCT No.: PCT/EP2017/070842
§ 371 (c)(1),
(2) Date: Feb. 20, 2019

(87) PCT Pub. No.: WO2018/036899
PCT Pub. Date: Mar. 1, 2018

(65) Prior Publication Data
US 2019/0183136 A1   Jun. 20, 2019

(30) Foreign Application Priority Data

Aug. 20, 2016  (EP) ..................................... 16185055

(51) Int. Cl.
*A23B 9/06* (2006.01)
*A23L 3/00* (2006.01)
(Continued)

(52) U.S. Cl.
CPC ................ *A23B 9/06* (2013.01); *A01C 1/08* (2013.01); *A23L 3/001* (2013.01); *A23L 3/26* (2013.01);
(Continued)

(58) Field of Classification Search
USPC ........................................................ 250/492.3
See application file for complete search history.

(56) References Cited

U.S. PATENT DOCUMENTS

| | | | |
|---|---|---|---|
| 4,734,586 A | 3/1988 | Crist et al. | |
| 4,959,500 A | 9/1990 | Kashiwagi et al. | |
| 5,801,387 A * | 9/1998 | Nablo | H01J 33/00 250/398 |
| 6,486,481 B1 | 11/2002 | Tigera | |
| 6,657,212 B2 | 12/2003 | Komori et al. | |

(Continued)

FOREIGN PATENT DOCUMENTS

| | | |
|---|---|---|
| DE | 38 16 946 A1 | 12/1988 |
| DE | 10 2012 209 434 A1 | 12/2013 |

(Continued)

*Primary Examiner* — Phillip A Johnston
(74) *Attorney, Agent, or Firm* — Davis & Bujold PLLC; Michael J. Bujold

(57) ABSTRACT

Devices (10) and methods for pasteurizing and/or sterilizing particulate material. The devices contain at least one electron source (20) for generating an electron beam and a treatment zone (19) in which the material is pasteurized and/or sterilized by the electron beam. The device (10) comprises a vibration surface (11) which vibrates to convey and individualize the material. The first vibration surface (11) has a plurality of grooves (12) into which the material is conveyed and individualized. The device (10) has a good channel (21) in which the material is pasteurized and/or sterilized by the electron beam in the region of the treatment zone (19). The device (10) has at least one auxiliary channel (22) through which a fluid flows between the electron source (20) and the good channel (21) and is separated from the good channel (21). A cartridge (24), for pasteurizing and/or sterilizing particulate material, is also disclosed.

22 Claims, 4 Drawing Sheets

(51) Int. Cl.

| | |
|---|---|
| *A61L 2/08* | (2006.01) |
| *B65B 37/04* | (2006.01) |
| *B65B 55/16* | (2006.01) |
| *G21K 5/08* | (2006.01) |
| *A23L 3/26* | (2006.01) |
| *A01C 1/08* | (2006.01) |
| *H01J 33/00* | (2006.01) |
| *B07C 5/04* | (2006.01) |
| *B07C 5/342* | (2006.01) |
| *B07B 13/11* | (2006.01) |
| *B07C 5/00* | (2006.01) |

(52) U.S. Cl.
CPC ............... *A23L 3/263* (2013.01); *A61L 2/087* (2013.01); *B65B 37/04* (2013.01); *B65B 55/16* (2013.01); *G21K 5/08* (2013.01); *H01J 33/00* (2013.01); *B07B 13/113* (2013.01); *B07C 5/00* (2013.01); *B07C 5/04* (2013.01); *B07C 5/342* (2013.01); *B07C 5/3425* (2013.01)

(56) References Cited

U.S. PATENT DOCUMENTS

| | | | |
|---|---|---|---|
| 6,724,003 | B1 | 4/2004 | Doi et al. |
| 6,734,383 | B1 | 5/2004 | Calcoen et al. |
| 6,745,512 | B1 | 6/2004 | Panzer et al. |
| 7,592,613 | B2 | 9/2009 | Kristiansson et al. |
| 8,714,363 | B2 * | 5/2014 | Bezuidenhout ......... B29C 31/02 209/247 |
| 9,736,977 | B2 | 8/2017 | Kotte et al. |

FOREIGN PATENT DOCUMENTS

| | | |
|---|---|---|
| EP | 0 104 938 A2 | 4/1984 |
| EP | 0 513 135 B1 | 8/1994 |
| EP | 0 705 531 A2 | 4/1996 |
| EP | 0 769 890 A1 | 1/1997 |
| EP | 1 080 623 A1 | 3/2001 |
| GB | 2 416 533 A | 2/2006 |
| JP | H11-101900 A | 4/1999 |
| JP | 2000-304900 A | 11/2000 |
| WO | 2006/010873 A1 | 2/2006 |

\* cited by examiner

DEVICES AND METHODS FOR PASTEURIZING AND/OR STERILIZING PARTICULATE MATERIAL, AND CARTRIDGE

This application is a National Stage completion of PCT/EP2017/070842 filed Aug. 17, 2017, which claims priority from European patent application serial no. 16185055.7 filed Aug. 20, 2016

FIELD OF THE INVENTION

This invention concerns devices and processes for pasteurizing and/or sterilizing particulate material by means of an electron beam and a cassette for insertion into such a device.

BACKGROUND OF THE INVENTION

Particulate goods are defined here and in the following as goods consisting inter alia of grains and/or flakes, whereby the particles can have a spherical, plate-shaped or angular shape. They may also be ground particles. Pasteurization and/or sterilization, for example, can kill or render harmless at least the majority of micro-organisms. In particular, a reduction of damaging micro-organisms by at least one, preferably at least five, particularly preferably at least seven orders of magnitude can be achieved.

A prior art device, for example, is known from EP 1 080 623 B1. This device contains vibrating conveyors with which seed can be separated into a transparent curtain. This curtain is then guided through an electron field generated by an electron accelerator which can, for example, sterilize the seed. A grid is used to keep the seed away from an exit window of the electron accelerator. However, this grid does not provide sufficient protection for the exit window, especially in the case of goods made of fine particles. In addition, some of the electrons are scattered away from the seed stream and thus cannot unfold their actual effect. Furthermore, the grating is difficult to clean and can easily be destroyed by the electron beam, which is why it only has a short service life.

From U.S. Pat. No. 5,801,387 A another prior art device is known. In the device according to that invention, a particle-shaped material is dosed into a horizontal air stream with a vibration conveyor and then exposed to an electron beam. A vacuum pump and a filter are then used to classify the material.

DE 10 2012 209 434 A1 discloses a device that separates and rotates a free-flowing product with the aid of a vibration conveyor and a rotating brush roller. The particles then pass freely falling through an electron field. However, this structure with rotating brush roller is structurally complex and prone to failure. In addition, the vibration conveyor and the brush roller do not always allow satisfactory separation. Furthermore, the brush roller is disadvantageous from a hygienic point of view, as it can only be cleaned cumbersomely of dust that accumulates during operation of the device. It can also happen that, in the case of a product with a wide particle size distribution, not all particles come into contact with the brush roller or the particles are accelerated differently. In addition, the brush roller can cause turbulence in the material, causing individual particles to hit the electron source and contaminate or even damage it.

In EP 0 513 135 B1 a device is disclosed with which seed is introduced into a vertical chute by means of rotary valves, where it is subjected to electron beams while falling vertically. However, even these rotary valves do not always permit satisfactory separation. In addition, the treatment is carried out in a vacuum, which makes the device expensive in terms of equipment and susceptible to faults and also causes high operating costs. In addition, the speed of the material is determined by the distance of the upper rotary valve from the electron source and cannot be varied.

A further device is known from EP 0 705 531 B1 which introduces the seed into a process chamber by means of an unspecified dosing device in which it falls vertically through an electron beam. However, even with this method, sufficient separation cannot be achieved.

The device disclosed in U.S. Pat. No. 6,486,481 B1 contains a vibrating table on which a polymeric material is moved and exposed to an electron beam. However, this is not done for pasteurization or sterilization purposes, but to reduce the molecular weight of the polymeric material.

SUMMARY OF THE INVENTION

It is therefore an aim of the present invention to overcome the disadvantages known from the prior art. In particular, devices and methods are to be provided for the effective and reliable pasteurization and/or sterilization of particulate material with a high throughput and as simple as possible. In particular, ozone generated by the electron beam should be removed as effectively and reliably as possible. In addition, the device, in particular an outlet window of an electron source, should preferably be protected from damage by the seed and be easy to clean, and the means for separation should also be easy to clean.

These and other aims re solved by the device according to the invention for pasteurizing and/or sterilizing particulate material. This device comprises a first vibrating surface, at least one electron source for generating an electron beam and a treatment zone downstream of the first vibrating surface. Here and in the following, the terms "downstream" and "upstream" refer to the direction of flow of the particulate material when the device is operated as intended. Consequently, a first unit is referred to as downstream of a second unit when it is passed by the good after the second unit when the device is properly operated. Similarly, a first unit is referred to as upstream of a second unit if, when the device is operated as intended, the goods pass through it before the second unit.

The first vibration surface is preferably aligned horizontally. Here and in the following, a (substantially) horizontal orientation is always understood to mean a (substantially) horizontal orientation when the device is installed as intended. It can be excited to vibrations in order to promote and isolate the good. In the treatment zone, the material can be pasteurized and/or sterilized by means of the electron beam.

According to the invention, the first vibrating surface has a large number of channels in which the material can be coveyed and separated. In principle, the channels can have any profile in a sectional plane perpendicular to the direction of flow, provided that the material can be conveyed and separated therein. For example, they can have an arched or an angular profile. The profile of a gutter may have a straight central section and two lateral sections extending obliquely upwards from the central section. The lateral sections of adjacent channels can meet at an edge.

Preferably at least one channel, preferably all channels, run substantially parallel to the direction of flow of the material. At least one channel, preferably all channels, may have a width ranging from 0.1 mm to 40 mm, preferably from 0.5 mm to 30 mm, particularly preferably from 1 mm to 20 mm.

Particles of the particulate material can be conveyed and separated in each of the channels. The separation takes place by dividing the particles of the particulate material into the channels.

It is preferable if the first vibrating surface is/are designed and arranged in such a way that it can be excited to vibrate and/or a possible downstream deflecting surface and/or a possible downstream slipping surface is/are designed and arranged in such a way that the material can be pasteurized and/or sterilized freely falling. The material is referred to as "freely falling" if the trajectories of the individual particles of the material are determined solely by their velocity, the force of gravity acting on them and, if applicable, a process gas surrounding the material. The process gas, for example, can be air. However, it is also conceivable that the process gas used is a gas that prevents ozone formation, such as nitrogen.

The electron beam can be used to treat not only the material itself, but also any process gas surrounding the material and/or other particles flowing with the material, such as dust.

The device has the advantage of having an inclined sliding surface downstream of the first vibration surface and upstream of the treatment zone, which is designed and arranged in such a way that the material can slide on it in the direction of the treatment zone. Due to the acceleration resulting from the slip, the particles of the material are further separated. In addition, the material can be fed to the treatment zone in a defined manner, in particular at a defined speed and trajectory. In particular, by selecting the length and inclination angle of the slide, the speed of the goods can be adjusted after leaving the slide.

The sliding surface preferably has at least one channel and preferably a large number of channels which are designed and arranged in such a way that the material can slide and be separated in them. This allows the speed and trajectory of the particles of the material to be further defined. With particular advantage, the channels of the sliding surface are adapted to the channels of the first vibrating surface in such a way that particles reaching the sliding surface from one and the same channel of the first vibrating surface reach one and the same channel of the sliding surface. This can prevent a turbulent movement of the particles, such as can occur, for example, with the brush roller disclosed in DE 10 2012 209 434 A1. In some applications the advantage can also be achieved that rotation of the particles of the material is prevented.

It has been found that the sliding surface is advantageously inclined downwards with respect to a horizontal line at an angle ranging from 45° to 85°, preferably from 55° to 75°, particularly preferred from 60° to 70° (if the device is properly installed). For many goods, angles in this area are large enough to accelerate the particles sufficiently over a tolerable length of the slide, and small enough to prevent them from lifting off the slide surface.

The at least one channel of the sliding surface can in principle have an arbitrary profile in a sectional plane perpendicular to the direction of flow, provided that the material can slide and be separated in it. For example, it may have an arched or angular profile. Preferably the at least one channel of the sliding surface runs substantially parallel to the flow direction of the material. The at least one channel of the sliding surface may have a width ranging from 40 mm to 3300 mm, preferably from 200 me to 600 mm, particularly preferably from 230 mm to 400 mm. The profile of a channel of the sliding surface may have a straight central section and two lateral sections extending obliquely upwards from the central section. If there are several channels, the lateral sections of adjacent channels may meet at one edge.

For many goods, it has also proved useful when the device has, downstream of the first vibrating surface and upstream of the treatment zone, in particular upstream of the slipping surface, a deflecting surface which is designed and arranged such that the goods can be deflected thereon and slide from the first vibrating surface to the slipping surface and/or in the direction of the treatment zone. In particular, if there is a sliding surface as described above, the particles of the material can be brought gradually and in a controlled manner to the inclination of the sliding surface. It is particularly advantageous if the sliding surface, in particular its at least one channel, is matched to the material and the first vibrating surface in such a way that the particles are guided on a parabolic path on which they would fall solely due to the effect of gravity.

With a special advantage, the deflection surface also has at least one channel, preferably a large number of channels, which are designed and arranged in such a way that the material car slide in them. This also has the effect here that the particles of the material can be guided in a controlled manner and no turbulence can occur and, in particular, a rotation of the particles can be prevented.

The at least one channel of the deflecting surface can in principle have an arbitrary profile in a section plane perpendicular to the direction of flow, provided that the material can slide in it. For example, it may have an arched or angular profile. The profile of a channel of the deflecting surface may have a straight central section and two lateral sections extending obliquely upwards from the central section. If there are several channels, the lateral sections of adjacent channels may meet at one edge. Preferably the at least one channel of the deflecting surface runs substantially parallel to the direction of flow of the material. The width of at least one channel of the deflecting surface may be in the range from 0.1 mm to 40 mm, preferably from 0.5 mm to 30 mm, particularly preferably from 1 mm to 20 mm.

With particular advantage, the channels of the deflection surface are adapted to the channels of the first vibration surface in such a way that particles reaching the deflection surface from one and the same channel of the first vibration surface reach one and the same channel of the deflection surface. Another particular advantage is that the channels of the sliding surface are adapted to the channels of the deflecting surface in such a way that particles from one and the same channel of the deflecting surface reach the deflecting surface in one and the same channel of the sliding surface.

However, in variation from the embodiments described above, it may also be useful for certain goods if the sliding surface and/or the deflecting surface have no grooves or if such a sliding surface and/or deflecting surface is not present at all. For example, the material can also be guided directly from the first vibration surface to the sliding surface, or it can be guided directly from the deflecting surface to the treatment zone. If, for example, the material consists of flakes, a deflecting surface can slow down and accumulate the flakes. To prevent this, it may be advantageous to dispense with a deflecting surface in the case of flakes. If, for example, the material is to fall vertically through the treatment zone, the deflecting surface and the sliding surface can be dispensed with.

Upstream of the first vibration surface, the device may have a substantially planar and preferably substantially horizontally aligned second vibration surface which is excitable to vibrations. With the help of such a second vibration surface, the throughput of the material can be controlled and pre-separation can already take place.

It is useful, during operation of the device, to excite the second vibrating surface to vibrations of a second amplitude smaller than a first amplitude of the vibrations to which the downstream first vibrating surface is excited. In this way the speed of the material is increased and further separation is achieved.

The vibrating surface(s) and/or the deflecting surface and/or the sliding surface may, for example, be made of a metal.

The at least one electron source can be known per se. The device may contain one or more electron sources. If several electron sources are present, they can be arranged opposite each other or one after the other with respect to the flow direction of the material.

Furthermore, it is also conceivable and within the scope of the invention that the device has several first vibration surfaces and/or several treatment zones. In this way, even more effective pasteurization and/or sterilization can be achieved. Alternatively, the material can be guided several times through one and the same treatment zone.

In a second independent aspect, the invention concerns a device for pasteurizing and/or sterilizing particulate material, also comprising at least one electron source for generating an electron beam and a treatment zone in which the material can be pasteurized and/or sterilized, in particular freely falling, by means of the electron beam. According to the second aspect, the device has a good channel in the area of the treatment zone in which the good can be pasteurized and/or sterilized by means of the electron beam. It also has at least one secondary channel through which a fluid can flow, which runs at least partially between the electron source and the good channel and is separated from the good channel fluid.

The fluid flowing through the secondary channel can be used to cool the electron source and in particular an exit window of the electron source. Alternatively or additionally, the fluid can be used to remove ozone generated by the electron beam. Neither this cooling nor this discharge of ozone from the secondary channel has any influence on the fluid flow in the good channel. Fluid separation is understood to mean that neither the fluid from the secondary channel car enter the good channel nor the good and any process gas surrounding the good can enter the secondary channel from the good channel. This prevents damage to or contamination of the electron source, in particular of an electron source exit window, by the material. The fluid car be a liquid or a gas, such as air. This overcomes the disadvantages of grids as described in EP 1 080 623 B1, for example.

It is advantageous to have a protective film between the electron source and the good channel which is at least partially permeable to the electron beam. This protective film preferably separates the good channel from the secondary channel. The secondary channel is also preferred at least partially between the electron source and the protective foil; the fluid in it is thus exposed to the electron beam during operation of the device. The protective film preferably consists of a metal such as titanium, aluminum, gold, silver or copper. The metal can also be an alloy. In some applications the protective film may be coated. Alternatively it is also conceivable and lies within the scope of the invention that the protective film consists of a plastic.

With particular advantage, the device comprises a cassette holder for holding a cassette, wherein the cassette at least partially delimits the good channel and the at least one secondary channel and comprises a film holder for holding the protective film. Another advantage of the electron source is that it can be moved, in particular pivoted and/or displaced, relative to the cassette holder in such a way that it can be moved away from the cassette. This simplifies access to the cassette and thus also to the protective film. The protective film can therefore be replaced more easily if it has been soiled or damaged by the material. The protective film can be detachably taken up from the film holder or can be taken up.

It has also proved useful if the device contains a suction device for extracting any process gas that surrounds the material. Advantageously, the suction device for sucking off the process gas is located downstream of the treatment zone, preferably at a distance from the treatment zone of 50 mm to 250 mm. In this way, ozone can be removed particularly effectively with the process gas, which has formed when passing through the treatment zone due to the impact of the electron beam.

However, it is also conceivable and within the scope of the invention that some goods flow through the treatment zone in a process gas flowing against the direction of flow of the goods and the extraction device for the extraction of process gas is arranged upstream of the treatment zone. This is particularly advantageous for heavier particles that are less affected by a process gas surrounding the material. This ensures that no untreated process gas can penetrate into a clean area downstream of the treatment zone in which the material should be pasteurized and/or sterilized during proper operation of the device. Recontamination can thus be prevented.

Downstream of the treatment zone, the device may also include a sorting device comprising a measuring unit and an ejection unit. The measuring unit and the ejection unit are designed in such a way that individual grains of the material can be ejected by means of the ejection unit on the basis of at least one property of the individual particles measured by the measuring unit. Such sorting facilities are known per se, for example from WO 2006/010873 A1. On the one hand, they can be used to expel individual particles that do not fulfil a given property. For example, sorting can be based on a measured size or color that is outside a specified tolerance range. On the other hand, the measuring unit can be designed in such a way that overlaps of the individual particles can be detected. Such an overlap may indicate that not all particles were sufficiently exposed to the electron beam as they passed through the treatment zone. These several overlapping particles can then be ejected for safety with the aid of the ejection unit.

It is also advantageous if the device has at least one gas outlet opening arranged downstream of the treatment zone for blowing a cleaning gas onto the material. In this way, remaining ozone can be removed. Alternatively, the cleaning gas can also be introduced upstream of the treatment zone, especially in the case of heavier particles, where the trajectory is less affected by the cleaning gas flow.

Another aspect of the invention concerns a cassette for insertion in a cassette holder of a device for pasteurizing and/or sterilizing particulate material containing at least one electron source for generating an electron beam. In particular, it may be a device as described above. The cassette contains delimiting surfaces for at least partially delimiting a good channel and at least one secondary channel of the device as well as a film holder for receiving a protective film which is at least partially permeable to the electron beam. The cassette can be inserted into the cassette holder in such a way that, in the region of a treatment zone, the device has a good channel in which the material can be pasteurized and/or sterilized by means of the electron beam, and in that the device has at least one secondary channel through which a fluid can flow, which secondary channel runs at least partially between the electron source and the good channel and is fluid-separated from the good channel. The boundary surfaces of the cassette then at least partially bound the good channel and at least one secondary channel.

The invention also includes a device as described above with a cassette holder and a cassette inserted therein as described above.

In another aspect, the invention also concerns a process for pasteurizing and/or sterilizing particulate material. This procedure can in particular be carried out with a device as described above. It contains the following steps:
a) Conveying and separating the material by means of a preferably substantially horizontally aligned first vibrating surface which is excited to vibrations and has a plurality of channels in which the material is conveyed and by means of which it is separated,
b) Generating an electron beam,
c) Pasteurization and/or sterilization of the material, in particular the free falling material, by means of the electron beam in a treatment zone.

With these methods, the advantages already mentioned above can be achieved.

An independent process for pasteurizing and/or sterilizing particulate material comprises the following steps:
b) Generation of an electron beam,
c) Pasteurization and/r sterilization of the material, in particular the free-falling material, by means of the electron beam in a treatment zone.

The material flows in the area of the treatment zone through a good channel in which it is pasteurized and/or sterilized by means of the electron beam. According to this independent aspect, a fluid flows through at least one secondary channel, which runs at least partially between the electron source and the good channel and is fluid-separated from the good channel. As already mentioned, with this fluid, which can be a liquid or a gas, ozone can be dissipated, which is produced by the electron beam. Alternatively or additionally, the fluid can also be used to cool the electron source, in particular an exit window. The fluid can flow through the secondary channel parallel or opposite to the flow direction of the material. The fluid used can be a gas that prevents the formation of ozone, such as nitrogen. The fluid flowing through the secondary channel may be identical to or different from the process gas flowing in the good channel. However, other directions of the fluid flow are also conceivable and are within the scope of the invention.

For many goods, in particular for a large number of spices, it has proved to be advantageous if the goods move through the treatment zone at a speed ranging from 1 m/s to 5 m/s, preferably from 2 m/s to 4 m/s, particularly preferably from 2 m/s to 3 m/s. The speed of the goods is determined by the speed of the spices. This speed can be adjusted, for example, by the length and angle of inclination of an upstream sliding surface. The higher the speed of the material, the greater the achievable throughput. In free fall, the speed is independent of the throughput, so that throughputs in the range of 100 kg/h to 1000 kg/h can be achieved at the same speed. The throughput only depends on the vibration of the vibration surface(s) and the dimensions and orientations of any deflection and slipping surfaces. Moreover, as the speed of the material increases, the probability of particle collisions with the electron source or the protective film decreases. On the other hand, the speeds must not be too high so that the material remains in the electron beam long enough to be pasteurized and/or sterilized.

Electrons of the electron beam should preferably have an energy in the range from 80 keV to 300 keV, preferably from 140 keV to 280 keV, especially preferred from 180 keV to 260 keV. Lower electron energies would not produce sufficient pasteurization and/or sterilization. Higher electron energies could not achieve significantly higher degrees of pasteurization and/or sterilization.

Advantageously, the material is exposed to the electron beam for a treatment time in the range of 5 ms to 25 ms. For a sufficient pasteurization and/or sterilization a certain minimum treatment time is necessary. Too long treatment times have shown no significant increase in pasteurization and/or sterilization and would also reduce throughput.

Another advantage is that the electron beam exposes the material to a radiation dose in the range from 1 kGy to 45 kGy, preferably from 8 kGy to 30 kGy, especially preferred from 10 kGy to 16 kGy.

The electron current density in the treatment zone is preferably in the range $10^{15}$ s$^{-1}$·cm$^{-2}$ to $2.77 \cdot 10^{15}$ s$^{-1}$·cm$^{-2}$.

It has also been shown that it is advantageous if process gas surrounding the product is extracted after pasteurization and/or sterilization. This allows ozone to be removed during pasteurization and/or sterilization.

The product can be a foodstuff such as cereals such as soya, breakfast cereals, snacks, nuts such as dried coconuts, almonds, peanut butter, cocoa beans, chocolate, chocolate liquid, chocolate powder, chocolate chips, cocoa products, pulses, coffee, seeds such as pumpkin seeds, spices (such as turmeric, particularly in slices), tea mixtures, dried fruit, pistachios, dry protein products, bakery products, sugar, potato products, pasta, baby food, dried egg products, soya products such as soya beans, thickeners, yeasts, yeast extracts, gelatine or enzymes.

Alternatively, the product may also be a pet food, such as pellets, feed for ruminants, poultry, aquatic animals (in particular fish) or pets, or compound feed.

It is, however, also conceivable and lies within the scope of the invention that the good is, for example, a plastic such as PET, for example in the form of flakes or pellets.

The device may have a clean area downstream of the treatment zone and, where appropriate, downstream of the suction device and/or the sorting device and/or the gas outlet, in which the material is pasteurized and/or sterilized during normal operation of the device.

Occasionally, electric discharges can occur in an electron source, which can damage the electron source. To counteract this, the electron source can be formed in such a way that it switches itself off in the event of a breakdown. As a result, however, the material is neither pasteurized nor sterilized and thus reaches the clean area, possibly even unnoticed.

To prevent this, the device can contain at least one radiation sensor that can be used to detect the intensity of the electron beam. Such radiation sensors for electron beams are known for example from the U.S. Pat. No. 6,657,212 or the U.S. Pat. No. 7,092,613. If the measured intensity falls below a pre-defined threshold value (which can also be an indication of an electric breakdown), the feed of the material can be stopped. Alternatively or additionally, the material may be discharged for pasteurization and/or sterilization at a later stage if necessary. For this purpose, the device may have an additional outlet for the material to be pasteurized and/or sterilized at a later stage. If the rejection is such that neither pasteurized nor sterilized material reaches the clean area, it is not necessary to stop the feeding of the material.

As soon as the clean area has been cleaned again after stopping the feed of the material and/or the rejection, further material car be fed into the device again or the rejection can be stopped.

BRIEF DESCRIPTION OF THE DRAWINGS

In the following, the invention is explained in more detail using certain embodiments and several drawings. It is shown in FIG. 1: a schematic side view of a device according to the invention.

DETAILED DESCRIPTION OF THE PREFERRED EMBODIMENTS

Figure 1:
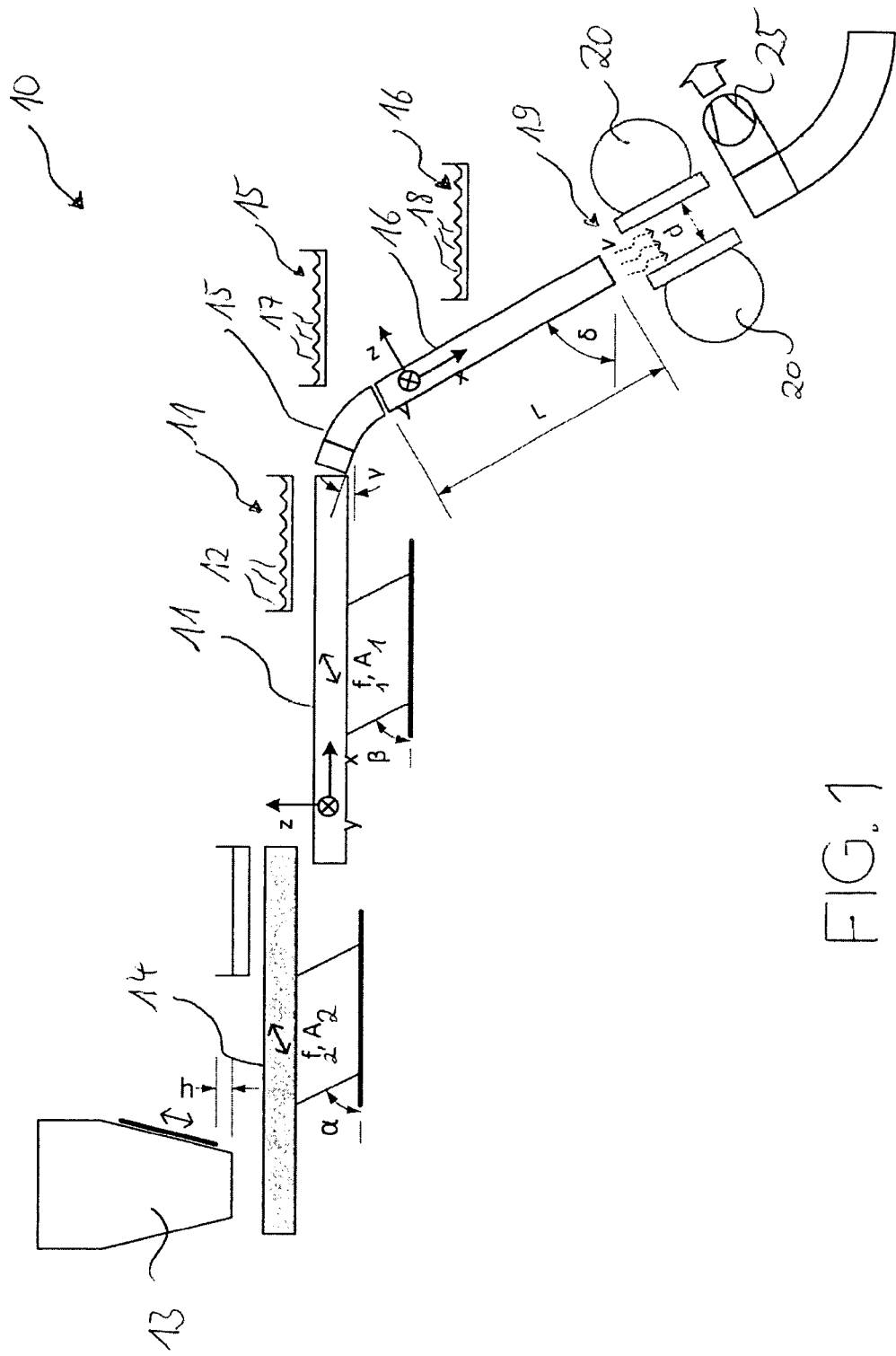

The device 10 shown in FIG. 1 is intended for pasteurizing and/or sterilizing particulate material such as a spice, sesame, almonds or peeled pistachios. It contains a dosing device 13 with which the material can be dosed onto a second vibrating surface 14. The second vibration surface 14 is horizontally aligned and level (if the device 10 is installed as intended). It can be excited to vibration with a frequency $f_2$ and an amplitude $A_2$ which runs at an angle $\alpha$ to the horizontal plane (if the device 10 is properly installed). With the aid of this second vibration surface 14, the throughput of the material can be controlled and pre-separation can also take place.

Downstream of the second vibration surface 14, the device 10 contains a horizontally aligned first vibration surface 11, which can be excited to vibrations with a frequency of $f_1$ and an amplitude of $A_1$ at an angle $\beta$ to the horizontal plane. This allows the material to be conveyed further downstream and separated. The first amplitude $f_1$ of the first vibration surface 11 is greater than the second amplitude f of the second vibration surface 14, which favours further separation. The first vibrating surface 1, in contrast to the first vibrating surface 14, contains a large number of channels 12 in which the material can be conveyed and separated. These channels 12 are shown in FIG. 1 in an insert showing the first vibration surface 11 in a sectional plane perpendicular to the direction of flow. The profile of gutters 12 has a straight central section with a with of 7.5 mm and two lateral sections extending obliquely upwards from the central section at an angle of 45°. The lateral sections of neighboring channels 12 meet at one edge. Two adjacent edges have a distance of 16.5 nm.

Downstream of the first vibration surface 11, the device 10 has a deflection surface 15. This is designed and arranged in such a way that the material is deflected onto it and can slide from the first vibration surface 11 to a sliding surface 16 described below. The deflection surface 15 also contains a large number of gutters 17, which are designed and arranged in such a way that the material can slide in them. The deflection surface 15 and its gutters 17 are matched to the material and the first vibration surface 11 in such a way that the particles of the material are essentially guided downstream on a parabolic path on which they would also fall solely due to the action of gravity. At the upstream end of the deflecting surface 15, this has an initial inclination γ. This allows a guidance and further separation of the particles of the material. The profile of the gutters 17 shown in a further insert also has a straight central section with a width of 7.5 mm and two lateral sections extending obliquely upwards from the central section at an angle of 45°. The lateral sections of neighboring gutters 17 meet at one edge. Two adjacent edges have a distance of 16.5 mm.

The aforementioned sliding surface 16, located downstream of the deflecting surface 15, is inclined with respect to a horizontal at an angle δ, which in the case of spices is advantageously 60°. The sliding surface 16 also has a large number of gutters 16, which are designed and arranged in such a way that the material car slide in them. The profile of the gutters 18 shown in a further insect also has a straight central section with a width of 7.5 mm and two lateral sections extending obliquely upwards from the central section at an angle of 45°. The lateral sections of neighboring gutters 17 meet at one edge. Two adjacent edges have a distance of 16.5 mm.

Further downstream, the device 10 contains a treatment zone 19, where the material is pasteurized and/or sterilized freely falling by means of an electron beam generated by two opposing electron sources 20.

The device 10 also contains a suction device 25 with which process gas, which surrounds the material, can be sucked off downstream of the treatment zone 19.

The following steps are performed for pasteurizing and/or sterilizing particulate material using this device 10:

By means of the second vibration surface 14 the throughput of the material is controlled and pre-separation takes place. In one step a) the material is conveyed and separated in the troughs 12 of the first vibration surface 11. By means of the electron sources 20 an electron beam is generated in one step b). In step c), the free-falling material is then pasteurized and/or sterilized by means of the electron beam in treatment zone 19.

In the case of spices, the material moves advantageously through treatment zone 19 at a speed of 2.5 m/s. This speed can be adjusted by the length and angle of inclination of the sliding surface 17. The electrons of the electron beam have an energy in the range of 80 keV to 300 keV, for example 250 keV. In treatment zone 19, the electron beam has an average current density in the range $10^{15}$ $s^{-1} \cdot cm^{-2}$ to 2.77-$10^{15}$ $s^{-1} \cdot cm^{-2}$. The material is exposed to the electron beam for a treatment time in the range of 5 ms to 25 ms, for example 15 ms. This exposes the material to radiation dose in the range from 1 kGy to 45 KGy, which may be 12 kGy, for example. After pasteurization and/or sterilization in treatment zone 19, the process gas surrounding the product is extracted by means of suction device 25 at a preferred extraction speed which is 1 to 1.5 times the speed of the product during pasteurization and/or sterilization.

Figure 2:
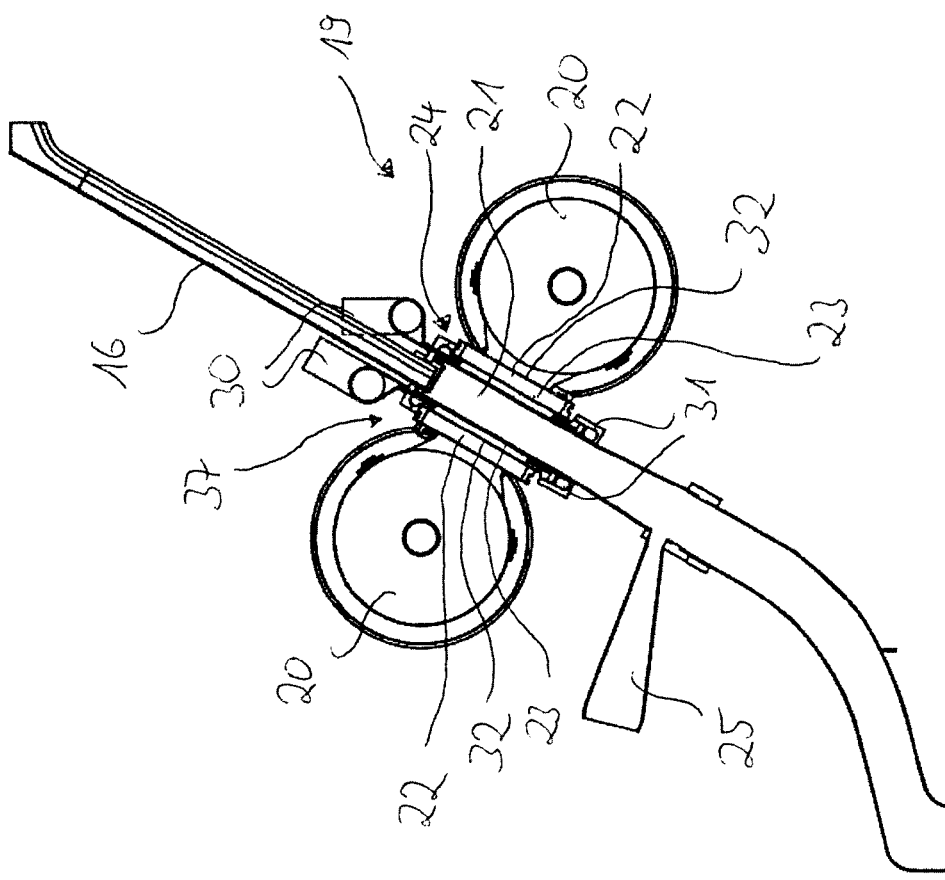
FIG. 2: a lateral view of a treatment zone of the device according to the invention.

FIG. 2 shows a detailed view of treatment zone 19. In the area of treatment zone 19, device 10 has a cassette 24 arranged between exit windows 32 of electron sources 20, a section of which is shown in more detail in FIG. 3. The cassette 24 is inserted in a cassette holder 37. The cassette 24 contains two film holders 35 for one titanium protective film 23 each, which are partially permeable to the electron beams. The cassette 24 contains several boundary surfaces 38, which together with the protective films 23 bound a good channel 21 in which the good can be pasteurized and/or sterilized by means of electron beams. Furthermore, the device 10 contains two secondary channels 22 in the area of the treatment zone 19. In the operating position shown in FIG. 2, these are bounded by boundary surfaces 38 of the cassette 24, the protective foil 23 and the exit windows 32 of the electron sources 20, which are not shown in FIG. 3, and thus run between the good channel 21 and the electron sources 20. The good channel 21 is fluid-separated from the secondary channels 23, inter alia by the protective foil 23.

Air can be introduced through inlet openings 30, which can flow through the secondary channels 23 parallel to the flow direction of the material. Downstream, the air can escape from outlet openings 31 again. On the one hand, this air flow enables the removal of ozone, which is generated by the electron beams, and on the other hand, it enables the cooling of the electron sources 20 and in particular their exit windows 32.

Figure 3:
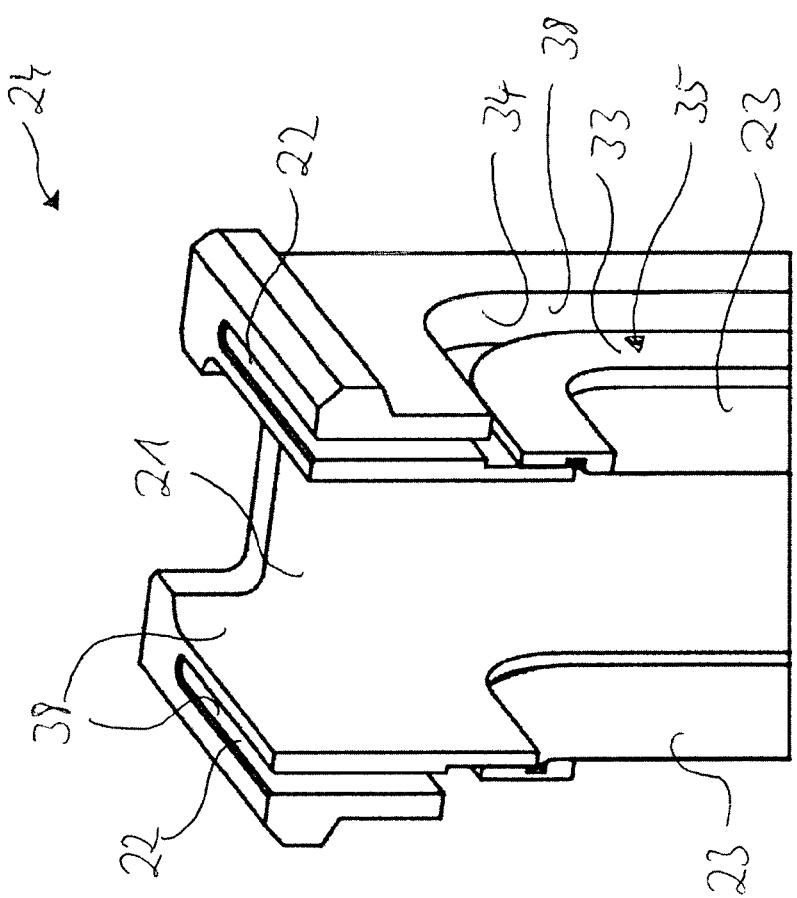
FIG. 3: a perspective cut detailed view of a cassette of the device according to the invention.

FIG. 3 shows a still detailed, cut and perspective view of cassette 24, in which the good channel 21, the two secondary channels 22 and the two protective foils 23 are visible. The good channel 21 is fluid-separated from the secondary channels 22 by the two protective foils 23. The protective films 23 are held by means of a respective clamping element 33, which form part of the film holder 35. On each side of the cassette 24 facing away from the good channel 21, a recess 34 is formed, which is closed in the operating position of the device 10 by exit windows 32 of the electron sources 20 and through which the electron beams can penetrate.

Figure 4:
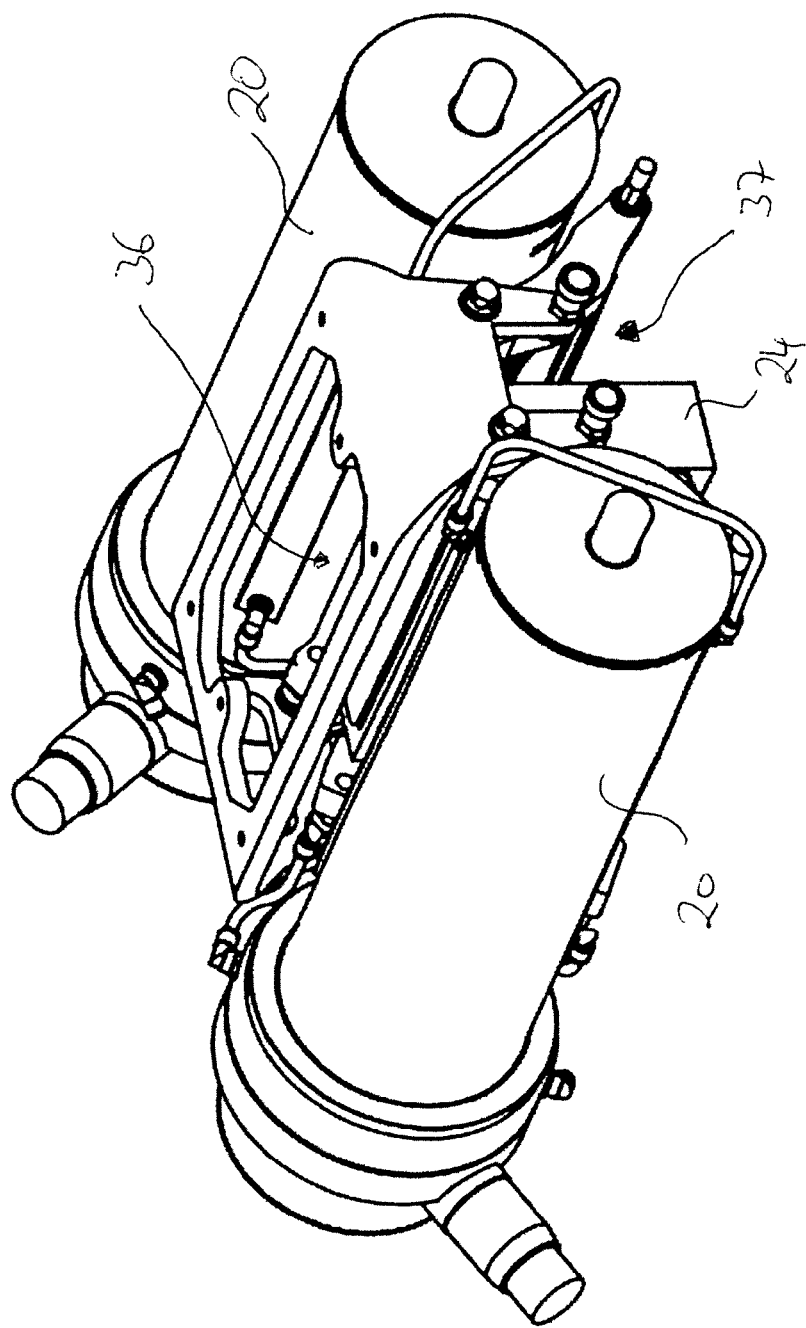
FIG. 4: a perspective view of the treatment zone of the device according to the invention.

FIG. 4 shows a part of the treatment zone 19 with the electron sources 20 and the cassette 24. The downstream end of the sliding surface 17 not shown here penetrates the opening 36 when the device 10 is mounted and is connected to the good channel 21. The electron sources 20 are arranged in such a way that they can be swiveled relative to the cassette holder 37 that they can be moved away from the cassette 24. In this way, the cassette 24 is easily accessible, especially if the protective foils 23 are dirty or damaged. The protective film 23 can be detachably attached to the film holder 35.

The invention claimed is:

1. An apparatus for pasteurizing or sterilizing particulate material comprising:
   a first vibration surface which is excitable by vibrations in order to convey and separate the material;
   at least one electron source for generating an electron beam;
   a treatment zone arranged downstream of the first vibration surface, in which the material can be pasteurized or sterilized by the electron beam;
   wherein the first vibrating surface comprises a plurality of channels in which the material is conveyed and by which the material is separated.

2. The apparatus according to claim 1, the apparatus having, downstream of the first vibrating surface and upstream of the treatment zone, an inclined slipping surface formed and arranged so that the material thereon slides toward the treatment zone.

3. The apparatus according to claim 2, wherein the sliding surface comprises at least one channel formed and arranged such that the material slides and is separated therein.

4. The apparatus according to claim 2, wherein the sliding surface is downwardly inclined, with respect to horizontal, at an angle which lies in a range from 45° to 85°.

5. The apparatus according to claim 1, wherein the apparatus has a defecting surface, downstream of the first vibration surface and upstream of the treatment zone, which is designed and arranged in such a way that the material is defected thereon and slides from the first vibration surface to the sliding surface and/or in a direction of the treatment zone.

6. The apparatus according to claim 5, wherein the deflecting surface comprises at least one channel which is designed and arranged in such a way that the material slides therein.

7. The apparatus according to claim 1, wherein the apparatus has, upstream of the first vibration surface, a substantially planar and substantially horizontally aligned second vibration surface which is excitable by vibrations.

8. The apparatus according to claim 1,
   the apparatus having, in a region of the treatment zone, a material channel in which the material is pasteurized or sterilized by the electron beam,
   wherein the apparatus has at least one secondary channel through which a fluid flows, which secondary channel runs at least partially between the electron source and the material channel and is fluid-separated from the material channel.

9. The apparatus according to claim 8, wherein a protective film, which is at least partially permeable to the electron beam, is arranged between the electron source and a good channel, which protective film separates the good channel from the secondary channel.

10. The apparatus according to claim 9, wherein the apparatus has a cassette receiver for receiving a cassette, the cassette at least partially delimits the material channel and the at least one secondary channel and contains a film receiver for receiving the protective film, and the source of electricity is movably arranged, relative to the cassette receiver, in such a way that the source of electricity is movable away from the cassette.

11. The apparatus according to claim 1, the apparatus includes suction means for sucking process gas surrounding the material downstream of the treatment zone.

12. The apparatus according to claim 1, wherein the apparatus has a sorting device downstream of the treatment zone, which sorting device contains a measuring unit and an ejection unit, which are designed in such a way that individual particles of the material are ejected by the ejection unit on a basis of at least one property of the particles measured by the measuring unit.

13. The apparatus according to claim 1, wherein the apparatus has at least one gas outlet opening, arranged downstream of the treatment zone, for blowing a cleaning gas onto the material.

14. A method for pasteurizing or sterilizing particulate material comprising the following steps:
   a) conveying and separating the material by a substantially horizontally oriented first vibrating surface which is excited so as to vibrate and has a plurality of channels in which the material is conveyed and by which the material is separated,
   b) generating an electron beam, and
   c) pasteurization or sterilization of the material by the electron beam in a treatment zone.

15. A method for pasteurizing or sterilizing particulate material comprising the following steps:
   d) generation of an electron beam,
   e) pasteurization or sterilization of the material by the electron beam in a treatment zone,
   wherein the material flows in the region of the treatment zone through a material channel in which the material is pasteurized or sterilized by the electron beam, a fluid flows through at least one secondary channel which runs at least partially between the electron source and the material channel and is fluid-separated from the material channel.

16. The method according to claim 14, wherein the material moves through the treatment zone at a speed which lies in a range from 1 m/s to 5 m/s.

17. The method according to claim 14, wherein the electrons of the electron beam have an energy ranging from 80 keV 300 keV.

18. The method according to claim 14, wherein the material is exposed to the electron beam for a treatment time ranging from 5 ms to 25 ms.

19. The method according to claim 14, wherein the material is exposed by the electron beam to a radiation dose ranging from 1 kGy to 45 kGy.

20. The method according to claim 14, wherein the electron beam in the treatment zone (19) has an average current density ranging from $10^{15}$ $s^{-1} \cdot cm^{-2}$ to $2.77 \cdot 10^{15}$ $s^{-1} \cdot cm^{-2}$.

21. The method according to claim 14, wherein process gas surrounding the material is sucked off after pasteurization or sterilization.

22. The method according to claim 14, wherein the material is selected from the group consisting of:

foodstuffs such as cereals such as soya, breakfast cereals, snacks, nuts such as dried coconuts, almonds, peanut butter, cocoa beans, chocolate, chocolate liquid, chocolate powder, chocolate chips, cocoa products, pulses, coffee, seeds such as pumpkin seeds, Spices (such as turmeric, especially in slices), tea mixtures, dried fruits, pistachios, dry protein products, bakery products, sugar, potato products, pasta, baby food, dried egg products, soya products such as soybeans, thickeners, yeasts, yeast extracts, gelatine or enzymes;

pet food, such as pellets, feed for ruminants, poultry, aquatic animals (in particular fish) or domestic animals, or compound feed; or plastic such as PET, for example in the form of flakes or pellets.

* * * * *